US012748110B2

(12) United States Patent
Fitzgerald et al.

(10) Patent No.: US 12,748,110 B2
(45) Date of Patent: Sep. 29, 2026

(54) BOVINE PATHOGEN ARRAY

(71) Applicants: Randox Laboratories Ltd, Crumlin Antrim (GB); Randox Teoranta, County Donegal (IE)

(72) Inventors: Peter Fitzgerald, Crumlin Antrim (GB); Ivan McConnell, Crumlin Antrim (GB); Ciaran Richardson, County Donegal (IE); John Lamont, Crumlin Antrim (GB)

(73) Assignees: Randox Laboratories Ltd., Antrim (GB); Randox Teoranta, Dungloe (IE)

( * ) Notice: Subject to any disclaimer, the term of this patent is extended or adjusted under 35 U.S.C. 154(b) by 1075 days.

(21) Appl. No.: 17/630,101

(22) PCT Filed: Jul. 26, 2020

(86) PCT No.: PCT/EP2020/071067
§ 371 (c)(1),
(2) Date: Jan. 25, 2022

(87) PCT Pub. No.: WO2021/018810
PCT Pub. Date: Feb. 4, 2021

(65) Prior Publication Data
US 2022/0349882 A1 Nov. 3, 2022

(30) Foreign Application Priority Data
Jul. 26, 2019 (GB) ...................................... 1910730

(51) Int. Cl.
*G01N 33/543* (2006.01)
*G01N 33/569* (2006.01)

(52) U.S. Cl.
CPC ... *G01N 33/54386* (2013.01); *G01N 33/5695* (2013.01); *G01N 33/56983* (2013.01); *G01N 2469/20* (2013.01)

(58) Field of Classification Search
CPC ....... G01N 33/54386; G01N 33/56983; G01N 2469/20; G01N 33/56994; G01N 2333/06; G01N 2333/183
See application file for complete search history.

(56) References Cited

U.S. PATENT DOCUMENTS

2004/0091939 A1* 5/2004 Cheung ............ G01N 33/54366 435/7.1
2005/0153382 A1* 7/2005 Zou .................. G01N 33/54386 435/7.93
2008/0138840 A1 6/2008 Collins et al.
2010/0196878 A1 8/2010 Vela Olmo et al.

FOREIGN PATENT DOCUMENTS

CN 1330271 A * 1/2002
CN 1946856 A 4/2007
GB 2324866 A 11/1998
WO 2005/118885 A1 12/2005
WO 2010/064164 A1 6/2010
WO 2013/003904 A1 1/2013
WO 2018/144571 A2 8/2018

OTHER PUBLICATIONS

Mayers J, Sawyer J. Development and evaluation of a multiplex enzyme-linked immunosorbent assay for the detection of antibodies to bovine respiratory diseases on the Meso Scale Discovery platform. Journal of Veterinary Diagnostic Investigation. 2012;24(4):725-729. doi:10.1177/1040638712446506 (Year: 2012).*
Grego E, Uslenghi F, Strasser M, et al. Development and Application of an Enzyme-Linked Immunosorbent Assay for Detection of Bovine Viral Diarrhea Antibody Based on Erns Glycoprotein . . . Journal of Veterinary Diagnostic Investigation. 2007;19(1):21-27. doi:10.1177/104063870701900104 (Year: 2007).*
Bertolotti, L., Muratore, E., Nogarol, C. et al. Development and validation of an indirect ELISA as a confirmatory test for surveillance of infectious bovine rhinotracheitis in vaccinated herds. BMC Vet Res 11, 300 (2015). https://doi.org/10.1186/s12917-015-0612-5 (Year: 2015).*
Nogarol, C., Decaro, N., Bertolotti, L. et al. Pestivirus infection in cattle dairy farms: E2 glycoprotein ELISA reveals the presence of bovine viral diarrhea virus type 2 in northwestern Italy. BMC Vet Res 13, 377 (2017). https://doi.org/10.1186/s12917-017-1305-z (Year: 2017).*
Nyman, AK.J., Ågren, E.C., Bergström, K. et al. Evaluation of the specificity of three enzyme-linked immunosorbent assays for detection of antibodies against *Salmonella* in bovine bulk milk. Acta Vet Scand 55, 5 (2013). https://doi.org/10.1186/1751-0147-55-5 (Year: 2013).*
Mayers J, Sawyer J. Development and evaluation of a multiplex enzyme-linked immunosorbent assay for the detection of antibodies to bovine respiratory diseases on the Meso Scale Discovery platform. Journal of Veterinary Diagnostic Investigation. 2012;24(4):725-729. (Year: 2012).*
Grego E, Uslenghi F, Strasser M, et al. Development and Application of an Enzyme-Linked Immunosorbent Assay for Detection of Bovine Viral Diarrhea Antibody Based on Erns Glycoprotein . . . Journal of Veterinary Diagnostic Investigation. 2007;19(1):21-27. (Year: 2007).*

(Continued)

*Primary Examiner* — Thomas J. Visone
*Assistant Examiner* — Samadhan Jaising Jadhao
(74) *Attorney, Agent, or Firm* — Gavrilovich, Dodd & Lindsey LLP

(57) ABSTRACT

The current invention provides a multiplex method for screening bovine samples for antibodies against several important pathogens. These pathogens include Bovine Viral Diarrhoea Virus (BVDV), Bovine Herpesvirus-1 (BoHV-1), *Mycobacterium* paratuberculosis (MAP), *Leptospira* species, *Neospora caninum* and *Fasciola hepatica*. This multiplex screening is enabled by substrates with immobilized pathogen antigens and offer multiple advantages for the routine testing of farm animals.

7 Claims, 4 Drawing Sheets

(56) References Cited

OTHER PUBLICATIONS

Bertolotti, L., Muratore, E., Nogarol, C. et al. Development and validation of an indirect ELISA as a confirmatory test for surveillance of infectious bovine rhinotracheitis in vaccinated herds. BMC Vet Res 11, 300 (2015). (Year: 2015).*
Nogarol, C., Decaro, N., Bertolotti, L. et al. Pestivirus infection in cattle dairy farms: E2 glycoprotein ELISA reveals the presence of bovine viral diarrhea virus type 2 in northwestern Italy. BMC Vet Res 13, 377 (2017). (Year: 2017).*
Nyman, AK.J., Ågren, E.C., Bergström, K. et al. Evaluation of the specificity of three enzyme-linked immunosorbent assays for detection of antibodies against *Salmonella* in bovine bulk milk. Acta Vet Scand 55, 5 (2013). (Year: 2013).*
Alkan et al 2018. Long-term study (2005-2010) on the vaccination with BoHV-1 glycoprotein E-deleted marker vaccine in selected two dairy herds in Turkey. Tropical animal health and production, 50(2), 353-363. (Year: 2018).*
Grego et al 2007. Development and application of an enzyme-linked immunosorbent assay for detection of bovine viral diarrhea antibody based on Erns glycoprotein expressed in a baculovirus system. Journal of Veterinary Diagnostic Investigation, 19(1), 21-27. (Year: 2007).*
Sayers RG, Sayers GP, Graham DA, Arkins S. Impact of three inactivated bovine viral diarrhoea virus vaccines on bulk milk p80 (NS3) ELISA test results in dairy herds. Vet J. Jul. 2015;205(1):56-61. (Year: 2015).*
Office Action, Application No. 202080063202.4, China National Intellectual Property Administration, May 6, 2025.
Alkan et al., "Long-term study (2005-2010) on the vaccination with BoHV-1 glycoprotein E-deleted marker vaccine in selected two dairy herds in Turkey," Trop Anim. Health Prod., 50(2):353-363, 2017.
Claridge et al., "Fasciola hepatica is associated with the failure to detect bovine tuberculosis in dairy cattle," Nature Communications, 3:853, 2012.
Chiodini et al., "Crohn's disease and the mycobacterioses: A quarter century later. Causation or simple association?" Critical Reviews in Microbiology, 38(1):52-93, 2012.
Nielsen et al., "A review of prevalences of paratuberculosis in farmed animals in Europe," Preventative Veterinary Medicine, 88:1-14, 2009.
Ridpath, Julia F., "Immunology of BVDV vaccines," Biologicals, 41:14-19, 2013.
Zoth et al., "Multiple recombinant ELISA for the detection of bovine viral diarrhoea virus antibodies in cattle sera," J. of Virological Methods, 138(1-2):99-108, 2006.
Gunster, Marco, International Search Report, European Patent Office, PCT/EP2020/071067, Nov. 30, 2020.
Gunster, Marco, Written Opinion of the ISA, European Patent Office, PCT/EP2020/071067, Nov. 30, 2020.
Office Action, China National Intellectual Property Administration, Application No. 202080063202.4, Jun. 24, 2024.

* cited by examiner

| | Sample Classification | | | | | | | | |
|---|---|---|---|---|---|---|---|---|---|
| | BVD | | IBR | | Paratuberculosis | Leptospirosis | Neospora Caninum | | Fasciola Hepatica |
| Sample ID | NS3 | Erns | IBR gB | IBR gE | MAP | Hardjo LipL32 | SR52 | P29 | CL1 |
| 16 | Pos | Pos | Pos | Neg | Pos | Pos | Pos | Pos | Neg |
| 23 | Neg | Pos | Neg | Neg | Neg | Neg | Neg | Neg | Neg |
| 38 | Pos | Pos | Pos | Neg | Neg | Pos | Pos | Pos | Neg |
| 63 | Pos | Pos | Pos | Neg | Neg | Neg | Pos | Pos | Neg |
| 78 | Pos | Pos | Pos | Pos | Pos | Pos | Pos | Pos | Neg |
| 110 | Pos | Pos | Neg | Neg | Neg | Neg | Pos | Pos | Neg |
| 111 | Pos | Pos | Neg | Neg | Neg | Neg | Pos | Neg | Neg |
| 138 | Pos | Pos | Pos | Neg | Neg | Pos | Pos | Pos | Neg |
| 142 | Neg | Neg | Neg | Neg | Neg | Neg | Pos | Pos | Neg |
| 150 | Neg | Pos | Neg | Neg | Neg | Neg | Pos | Pos | Neg |
| 154 | Pos | Pos | Pos | Neg | Neg | Pos | Pos | Pos | Neg |
| 163 | Pos | Pos | Neg | Neg | Neg | Neg | Pos | Pos | Neg |
| 200 | Pos | Neg | Neg | Neg | Neg | Pos | Pos | Pos | Neg |
| 222 | Pos | Pos | Neg | Neg | Pos | Pos | Pos | Pos | Neg |
| 224 | Neg | Pos | Neg | Neg | Neg | Neg | Neg | Neg | Neg |
| 231 | Neg | Neg | Neg | Neg | Neg | Neg | Neg | Neg | Neg |
| 241 | Pos | Pos | Pos | Neg | Neg | Neg | Pos | Pos | Neg |
| 297 | Pos | Pos | Pos | Neg | Pos | Pos | Pos | Pos | Neg |
| 408 | Pos | Pos | Pos | Pos | Pos | Pos | Pos | Pos | Neg |
| 860 | Pos | Pos | Neg | Neg | Neg | Neg | Neg | Pos | Neg |
| 954 | Neg | Pos | Neg | Neg | Neg | Neg | Neg | Neg | Neg |
| 1140 | Pos | Pos | Pos | Neg | Pos | Pos | Pos | Neg | Neg |
| 1218 | Neg | Pos | Pos | Pos | Neg | Pos | Pos | Neg | Neg |
| 1373 | Neg | Neg | Neg | Neg | Neg | Neg | Pos | Pos | Neg |
| 1464 | Pos | Pos | Neg | Neg | Neg | Neg | Pos | Pos | Neg |
| 1485 | Neg | Neg | Neg | Neg | Neg | Neg | Pos | Neg | Neg |
| 1497 | Neg | Neg | Neg | Neg | Neg | Neg | Pos | Pos | Neg |
| 1528 | Neg | Neg | Neg | Neg | Neg | Neg | Pos | Neg | Neg |
| 1530 | Neg | Neg | Neg | Neg | Neg | Neg | Pos | Neg | Neg |
| 1534 | Neg | Neg | Neg | Neg | Neg | Neg | Pos | Pos | Neg |
| 1552 | Neg | Neg | Neg | Neg | Neg | Neg | Neg | Neg | Neg |
| 1576 | Neg | Neg | Neg | Neg | Neg | Neg | Pos | Pos | Neg |
| 1597 | Neg | Neg | Neg | Neg | Neg | Neg | Neg | Neg | Neg |

FIG. 3

| Sample ID | BVD NS3 | BVD Erns | IBR gB | IBR gE | MAP | HardjoLipL32 | Neospora Caninum SRS2 | Neospora Caninum P29 | Fasciola Hepatica CL1 |
|---|---|---|---|---|---|---|---|---|---|
| 16 | 717.1% | 241.5% | 801.6% | 2.4% | 126.3% | 2625.8% | 1079.7% | 237.9% | 1.9% |
| 23 | 10.4% | 61.4% | 35.9% | 0.0% | 0.0% | 46.5% | 44.1% | 15.6% | 0.0% |
| 38 | 2321.6% | 1479.2% | 66.7% | 6.2% | 13.6% | 172.5% | 98.5% | 160.5% | 0.0% |
| 63 | 250.2% | 51.8% | 70.8% | 0.0% | 0.0% | 31.0% | 862.0% | 1806.5% | 1.0% |
| 78 | 3592.9% | 1656.2% | 269.4% | 97.4% | 55.9% | 114.4% | 3352.3% | 1198.4% | 0.0% |
| 110 | 3587.2% | 1919.9% | 16.7% | 0.0% | 5.6% | 0.0% | 558.5% | 281.1% | 0.0% |
| 111 | 4494.7% | 1782.1% | 23.6% | 2.9% | 7.8% | 9.5% | 89.5% | 29.1% | 3.4% |
| 138 | 349.7% | 282.3% | 1419.6% | 4.6% | 37.6% | 68.0% | 312.6% | 351.4% | 0.8% |
| 142 | 0.0% | 0.0% | 21.6% | 0.0% | 8.8% | 5.5% | 1711.9% | 739.4% | 0.0% |
| 150 | 13.0% | 81.9% | 37.7% | 3.8% | 0.0% | 29.5% | 412.2% | 623.7% | 0.0% |
| 154 | 1584.1% | 200.8% | 105.6% | 14.5% | 30.6% | 79.3% | 1474.2% | 477.8% | 0.7% |
| 163 | 3609.5% | 4992.1% | 34.6% | 4.1% | 29.4% | 47.0% | 267.4% | 167.0% | 4.5% |
| 200 | 280.7% | 37.0% | 23.2% | 5.2% | 0.0% | 59.5% | 76.9% | 98.8% | 0.0% |
| 222 | 181.6% | 59.8% | 0.0% | 2.1% | 157.7% | 81.8% | 201.1% | 72.0% | 0.0% |
| 224 | 48.8% | 2439.8% | 0.0% | 0.0% | 0.0% | 10.3% | 0.0% | 0.0% | 0.0% |
| 231 | 0.0% | 0.0% | 0.0% | 0.0% | 0.0% | 0.0% | 0.0% | 0.0% | 0.0% |
| 241 | 4450.2% | 6778.5% | 217.9% | 8.4% | 0.0% | 31.2% | 89.1% | 66.9% | 0.0% |
| 297 | 616.0% | 55.7% | 822.4% | 12.8% | 86.7% | 64.5% | 892.7% | 347.3% | 3.8% |
| 408 | 7977.5% | 4996.5% | 1092.5% | 105.0% | 62.5% | 2833.3% | 457.5% | 132.0% | 10.0% |
| 860 | 94.0% | 350.4% | 0.0% | 0.0% | 0.0% | 0.0% | 3.9% | 53.2% | 0.0% |
| 954 | 0.0% | 407.2% | 48.2% | 4.4% | 0.0% | 15.0% | 7.6% | 2.8% | 0.0% |
| 1140 | 114.1% | 234.7% | 200.8% | 23.1% | 200.6% | 94.0% | 1642.3% | 42.9% | 0.0% |
| 1218 | 45.4% | 92.2% | 107.4% | 53.4% | 8.8% | 108.5% | 737.5% | 26.5% | 0.0% |
| 1373 | 0.0% | 10.9% | 0.0% | 2.3% | 0.0% | 0.0% | 342.8% | 259.7% | 0.0% |
| 1464 | 90.2% | 78.3% | 23.6% | 6.4% | 19.0% | 38.5% | 134.0% | 56.3% | 0.0% |
| 1485 | 6.2% | 14.1% | 13.6% | 7.6% | 0.0% | 11.6% | 1063.8% | 47.3% | 0.0% |
| 1497 | 27.2% | 8.0% | 0.0% | 4.7% | 0.0% | 15.3% | 911.3% | 387.4% | 0.0% |
| 1528 | 5.0% | 0.0% | 9.2% | 2.6% | 0.0% | 0.0% | 455.2% | 31.0% | 0.0% |
| 1530 | 0.0% | 0.0% | 0.0% | 0.0% | 0.0% | 0.0% | 212.9% | 42.5% | 0.0% |
| 1534 | 0.0% | 12.3% | 12.2% | 0.0% | 0.0% | 0.0% | 292.4% | 83.0% | 0.0% |
| 1552 | 0.0% | 0.0% | 6.1% | 0.0% | 0.0% | 0.0% | 6.5% | 5.1% | 0.8% |
| 1576 | 0.0% | 0.0% | 13.1% | 2.9% | 4.2% | 0.0% | 151.9% | 423.4% | 0.0% |
| 1597 | 6.6% | 0.0% | 12.2% | 3.4% | 3.8% | 7.0% | 31.8% | 4.0% | 0.0% |

FIG. 4

BOVINE PATHOGEN ARRAY

CROSS REFERENCE TO RELATED APPLICATIONS

This application is a U.S. National Stage Application filed under 35 U.S.C. § 371 and claims priority to International Application No. PCT/EP2020/071067, filed Jul. 26, 2020, which application claims priority to Great Britain Application No. 1910730.9, filed Jul. 26, 2019, the disclosures of which are incorporated herein by reference.

BACKGROUND

Veterinary in vitro diagnostic tests are essential tools for establishing animal health status and identifying disease outbreaks. An accurate and prompt diagnosis will deliver countless benefits including: Minimising economic losses, maximising productivity, significantly improving animal welfare, reducing antibiotic/anthelmintic resistance, delivering competitive advantages/assurances regarding trade and supporting the Global One Health Initiative.

Serological detection of bovine infectious diseases is routinely performed using singleplex ELISA which is time consuming, expensive and requires large sample volumes.

Infectious Bovine Rhinotracheitis (IBR) is a highly contagious, infectious respiratory disease that is caused by Bovine Herpesvirus-1 (BoHV-1). It affects cattle of all ages and is characterised by an acute inflammation of the upper respiratory tract. The virus can also cause conjunctivitis, abortions, encephalitis, and generalised systemic infections. Once they have recovered from the initial infection, animals develop a life-long latent phase meaning that infected animals have a constant risk of infecting a herd.

There is no direct treatment available for IBR. Once identified, infected animals are isolated from the rest of the herd and treated with anti-inflammatory drugs and antibiotics for secondary infections if necessary. Carrier cattle also need to be identified and removed from the herd.

Control of IBR relies heavily on the use of vaccines. Current available vaccines include modified-live-virus (MLV) vaccines and inactivated or killed-virus (KV) vaccines. The use of marker vaccines is preferred since they have specific antigens deleted and so the antibody they stimulate can be distinguished from antibodies which result from a naturally acquired infection.

Bovine viral diarrhoea (BVD) is another economically significant disease of cattle and other ruminants and is caused by the Bovine viral diarrhoea virus (BVDV). It is a common cause of respiratory and reproductive issues within a herd. Congenital infection of a foetus can lead to resorption, abortion or stillbirth, and even if a BVDV infected calf survives the in utero infection they may be weak and abnormally small. The infection will also persist throughout their life and they can continuously shed BVDV into the farm environment.

Treatment of BVD is limited primarily to supportive therapy. Once identified, infected animals should be culled and diagnostic testing is important to identify persistently infected animals. As with IBR, both live and killed-virus vaccines are available for BVD. Both killed (inactivated) and modified live BVD virus vaccines are available. Following vaccination using inactivated vaccines, the humoral antibody response is largely directed against BVD structural proteins e.g. Erns and E2 and a reaction against non-structural proteins e.g. NS3 is largely reduced or non-existent (Ridpath 2013). Furthermore, modified live vaccines may be attenuated through the deletion of viral protein e.g. Erns, hence the detection of antibodies against this protein may only occur as a result of natural infection.

Neosporosis is an infection caused by the protozoa *Neospora caninum* and which is a major cause of abortion in cattle, resulting in significant economic losses and decreases in production. Different stages of infection including tachyzoite (acute infection) and bradyzoite (chronic infection) occur. There are currently no treatments for bovine neosporosis with any proven benefit and so control is based on biosecurity and management practices. Infected cattle need to be identified by diagnostic testing and removed from the herd. All cattle with antibodies to *Neospora* are sources of infection to their calves, have a significantly increased risk of abortion, and, on average, produce less milk than antibody negative cows. Before a diagnosis of neosporosis is made it is important to eliminate other causes of abortion in a herd, particularly BVD or leptospirosis.

Johne's disease, or paratuberculosis, is a chronic enteritis of ruminants caused by *Mycobacterium avium* subspecies paratuberculosis (MAP). It is thought that over half of European dairy cattle herd may be infected (Nielson & Taft, 2009) and there is increasing concern that this bacteria's presence in the human food chain is a causative factor in Crohn's Disease (Chiodini et al, 2012).

Because of the slow, progressive nature of the infection, signs of Johne's disease may not show up until years after the initial infection. When they finally do occur, the signs are long-lasting diarrhoea and weight loss despite good appetite. Once clinical signs appear the animal will not recover and will continue to deteriorate. As is the case with the pathologies mentioned above, currently there is no treatment for Johne's disease. Vaccines are available but preventative methods can be more effective.

Only a small proportion of animals develop overt clinical signs that are easily identified allowing them to be removed from the herd. The identification of subclinical disease in animals, which can shed the organism over long periods and thus be the source of infection for other members of the herd, is crucial for disease control. Animals are usually infected at a young age, and it can take years until clinical signs appear. PCR and serology tests are available for *M. paratuberculosis.*

Leptospirosis is a zoonotic disease, caused by bacteria of genus *Leptospira*. Numerous serovars are found in cattle and their prevalence varies depending on geographical location. These serovars include hardjo, *pomona, canicola*, icterohaemorrhagiae, and grippotyphosa. *Leptospira hardjo-bovis* is the only host-adapted Lepto serovar in cattle and can infect animals at any age, including young calves.

Because cattle are the maintenance host for hardjo-*bovis*, infection with this serovar will often produce a carrier state in the kidneys associated with long-term urinary shedding.

In addition, infections with hardjo-*bovis* can persist in the reproductive tract. The infertility that can result from persistent reproductive tract infections is perhaps the most economically damaging aspect of leptospirosis. Low antibody titres are typically associated with hardjo-*bovis* infections, making detection and diagnosis difficult.

Leptospirosis caused by non-host-adapted *Leptospira* serovars can be severe, particularly in calves, with symptoms including high fever, anaemia, red urine, jaundice, and sometimes death in three to five days. In older cattle, the initial symptoms such as fever and lethargy are often milder and often go unnoticed. In addition, leptospirosis is not usually fatal for older animals. Lactating cows which are infected produce less milk, and, for a week or more, the milk they produce is thick and yellow. In pregnant cow's infections can result in embryonic death, abortions, stillbirths, retained placenta, and the birth of weak calves. Abortions usually occur three to ten weeks after infection. Antibiotic therapy can be prescribed for animals with leptospirosis and also to eliminate persistent infections.

The helminth parasite *Fasciola hepatica* causes liver fluke disease (fascioliasis) in cattle and other ruminants and is also an important human pathogen. Infections in cattle result in mortality losses, reduced weight gain, reduced milk production and reduced carcass quality. As well as direct effects from the parasitic infection, *Fasciola hepatica* and other helminths impair their hosts immune response leaving them more susceptible to other infections and affecting the sensitivity of serological tests. Indeed, *Fasciola hepatica* infection has been associated with failure to detect bovine tuberculosis in dairy cattle (Claridge et al, 2012).

Fast and accurate diagnosis of infectious diseases in cattle is vital for disease control and eradication from herds and for the treatment of affected individuals. Commercially available ELISAs are designed to detect a single biomarker and therefore a multiplex test, which allows samples to be screened for multiple pathogens in a single assay, would offer multiple advantages for routine testing. Provided herein are methods, substrates and kits to address this need.

REFERENCES

Ridpath 2013. *Biologicals.* 2013 January; 41(1):14-9. PMID: 22883306

Nielson & Taft 2009. *Prev Vet Med.* 2009 Jan. 1; 88(1):1-14. PMID: 18817995

Chiodini et al 2012. *Crit Rev Microbiol.* 2012 February; 38(1):52-93. PMID: 22242906

Claridge et al 2012. *Nat Commun.* 2012 May 22; 3:853. PMID: 22617293

DESCRIPTION OF DRAWINGS

FIG. 3 An example of the basic positive or negative output for the multiplex array.

FIG. 4 An example of the percentage positivity output for the multiplex array.

SUMMARY OF INVENTION

Figure 1:
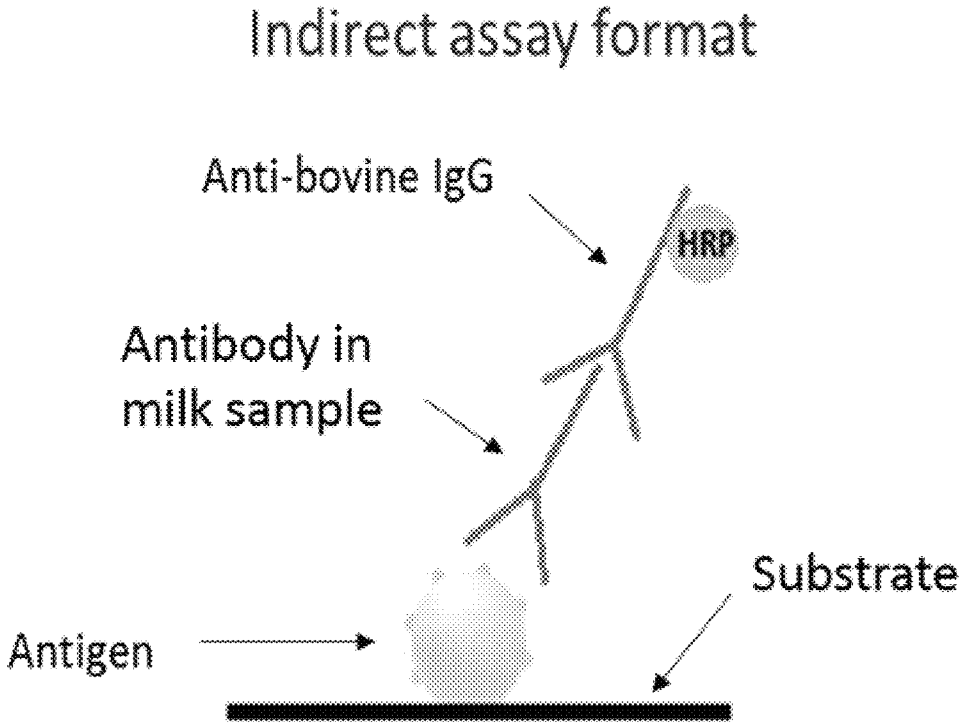
FIG. 1 illustrates the indirect ELISA format of the current arrays. An antigen from a pathogen is immobilized on a substrate which is contacted with the bovine sample. If the sample contains any antibodies to the antigen they will bind and these can be detected using a labelled detection antibody.

A first aspect of the current invention is a multiplex method for screening bovine samples for antibodies against a number of important pathogens. These pathogens include Bovine Viral Diarrhoea Virus (BVDV), Bovine Herpesvirus-1 (BoHV-1), *Mycobacterium* paratuberculosis (MAP), *Leptospira* species, *Neospora caninum* and *Fasciola hepatica.*

A second aspect of the current invention is a substrate which enables such multiplex detection. Said substrate has two or more antigens selected from the list BVDV NS3, BVDV Erns, BVDV E2, BoHV-1 glycoprotein B, BoHV-1 glycoprotein E, MAP PPA, *Leptospira* hardjo LipL32, *Neospora caninum* SRS2, *Neospora Caninum* SAG1 and *Fasciola hepatica* Cathepsin L1.

A third aspect of the current invention is a method for screening bovine samples for antibodies against *Mycobacterium* paratuberculous comprising bringing the sample into contact with a substrate onto which is immobilized an antigen of *M. paratuberculosis* and an assay buffer containing *Mycobacterium phlei.*

A fourth aspect of the current invention is a method for differentiating BoHV-1 infected from vaccinated animals (DIVA) using a substrate with the immobilized target antigens glycoprotein B and glycoprotein E and BVDV infected from vaccinated animals (DIVA) using a substrate with the immobilized target antigens NS3 and Erns.

A fifth aspect of the current invention is a normalisation method for a multiplex array which enables ease of result interpretation and removes batch to batch variance. Additional information of the percentage positivity or negativity of each sample compared to controls has the potential to indicate stage of infection, influence treatment pathways and enable the identification of animals requiring follow-up tests or monitoring.

DETAILED DESCRIPTION

Unless otherwise stated, technical terms are used according to the conventional usage as known to those skilled in the art.

In a first embodiment, the current invention comprises a method for screening a bovine sample for antibodies against multiple pathogens, said method comprising; (a) contacting the bovine sample with a substrate onto which is immobilized two or more antigens of two or more pathogens (b) washing off unbound sample (c) detecting any antibodies in the sample which are bound to the immobilized antigens on the substrate using a labelled detector antibody.

In a preferred embodiment, two or more pathogens are selected from the list consisting of BVDV, BoHV-1, *Mycobacterium* paratuberculosis, a *Leptospira* species, *Neospora caninum* and *Fasciola hepatica*. Any two, three, four or five pathogen combinations, or indeed a combination of all six pathogens is disclosed herein. The method comprises contacting the bovine sample with a substrate onto which is immobilized two or more antigens of two or more pathogen targets, preferably, when one of the pathogen targets is BVDV the antigen immobilized is one or more of NS3, Erns and E2. This can depend on sample type, for example, when the sample is milk the preferred BVDV antigens are N53 and Erns. However, when the sample is serum the preferred antigens are NS3 and E2. When one of the pathogen targets is BoHV-1 the antigens immobilized are preferably gB and gE. When one of the pathogen targets is *Mycobacterium* paratuberculosis the immobilized antigen is preferably MAP PPA. When one of the pathogen targets is a *Leptospira* species the immobilized antigen is preferably LipL32. When one of the pathogen targets is *Neospora caninum* the immobilized antigen is preferably one or both of SRS2 and SAG1. When one of the pathogen targets is *Fasciola hepatica* the immobilized antigen is preferably Cathepsin L1.

In one preferred embodiment, the target pathogens include at least BVDV, BoHV-1 and *Mycobacterium* paratuberculosis. In another preferred embodiment, the target pathogens include at least BVDV, BoHV-1 and *Neospora caninum.* In a further preferred embodiment, the target pathogens include at least BVDV, *Neospora caninum* and a *Leptospira* serovar.

The term "screening" as used herein means assaying a sample for the presence or absence of antibodies towards pathogens. These antibodies may be as the result of vaccination against a certain pathogen or from a naturally acquired infection with a certain pathogen.

The term "bovine" as used herein refers to species within the biological subfamily Bovinae. More particularly it refers to species in the Genus *Bos*, even more particularly to the domestic cattle, *Bos taurus.*

The "sample" referred to herein includes any suitable sample obtained from a bovine subject in which antibodies to a pathogen may be detected, such samples include milk, whole blood, plasma, serum, urine, saliva, semen, cerebrospinal fluid and tissue extracts. When the sample is whole milk, samples may be centrifuged or left to sit so that the cream separates from the lactoserum. The lactoserum can then be used as the test sample. Preferred samples are milk and serum.

The term "antibody" refers to an immunoglobulin which specifically recognises an epitope on a target, as determined by the binding characteristics of the immunoglobulin variable domains of the heavy and light chains (VHs and VLs), more specifically the complementarity-determining regions (CDRs). Many potential antibody forms are known in the art, and are included within the above definition. These may include, but are not limited to, a plurality of intact monoclonal antibodies or polyclonal mixtures comprising intact monoclonal antibodies, antibody fragments (for example Fab, Fab', F(ab')2 and Fv fragments, linear antibodies, single chain antibodies and multispecific antibodies comprising antibody fragments), single chain variable fragments (scFvs), multispecific antibodies, chimeric antibodies, humanised antibodies and fusion proteins comprising the domains necessary for the recognition of a given epitope on a target. An antibody may comprise γ, δ, α, μ and ε type heavy chain constant domains, wherein an antibody comprising said domains is designated the class IgG, IgD, IgA, IgM or IgE respectively. Classes may be further divided into subclasses according to variations in the sequence of the heavy chain constant domain (for example IgG1-4). Light chains are designated either κ or λ class, depending on the identity of the constant region. Antibodies may also be conjugated to various labels that enable detection, including but not limited to radioactive markers, DNA, RNA, fluorescent molecules, or an enzyme which converts a substrate such that its absorbance or chemiluminescence can be detected. Antibodies may also be modified to enable their immobilization within a substrate in a specific or non-specific orientation.

Detector antibodies may comprise detectable labels that can be visualised once a binding event has occurred. Non-limiting examples of detectable labels include radionucleotides, fluorophores, dyes, or enzymes that convert a substrate such that its absorbance or chemiluminescence signal can be detected. A preferred detectable label is horseradish peroxidase (HRP). Detector antibodies may be any antibody with sufficient cross-reactivity to the bovine antibodies which are targeted in the current assays. For example, suitable detector antibodies could be anti-IgG or anti-IgM antibodies derived from sheep, goats, rabbits or mice. Detector antibodies may also be any antibody with sufficient cross-reactivity to detect antibodies in controls which were raised in another species. Preferably the same detector antibody is used for all arrays in the multiplex format. In preferred embodiments, the detector antibodies are anti-bovine IgG or anti-bovine IgM.

The term "NS3" used herein refers to Non-structural protein NS3 of Bovine viral diarrhoea virus (Uniprot accession number P19711).

The term "Erns" as used herein refers to the BVDV glycoprotein Erns found on the surface of the virion (Uniprot accession number P19711).

The term "E2" as used herein refers to the BVDV glycoprotein E2 (Uniprot accession numberP19711).

The term "gB" as used herein refers to envelope glycoprotein B of Bovine herpesvirus 1 (Uniprot accession number P12640). The term "gE" as used herein refers to envelope glycoprotein E of Bovine herpesvirus 1 (Uniprot accession number Q08101).

The term "PPA" as used herein refers to protoplasmic antigen—of *Mycobacterium avium*, which is the most common antigen used for the serological detection of PTB.

The term "Lipl32" as used herein refers to the *Leptospira* major outer-membrane protein LipL32 (Uniprot accession number Q04SB6). The term "*Leptospira* species" as used herein refers to any bacteria from the genus *Leptospira* capable of infecting in cattle. These include, but are not limited to, *Leptospira borgpetersenii* serovar hardjo, *Leptospira interrogans* serovar hardjo and *Leptospira interrogans* serovar Pomona.

The term "SRS2" as used herein refers to the *Neospora caninum* surface antigen-related sequence 2 (Uniprot accession number Q9TVP5), also known as p35.

The term "SAG1" as used herein refers to the *Neospora caninum* surface antigen 1 (Uniprot accession number Q9TVV8), also known as p29.

The term "Cathepsin L1" as used herein refers to the *Fasciola hepatica* Cathepsin L1 (Uniprot accession number Q7JNQ9).

The current invention also provides a substrate which enables the multiplex screening of bovine samples for antibodies to pathogens. Onto the surface of said substrate are immobilized two or more antigens, preferably from two or more pathogens, selected from the list consisting of BVDV NS3, BVDV Erns, BoHV-1 glycoprotein B, BoHV-1 glycoprotein E, MAP PPA, *Leptospira* hardjo LipL32, *Neospora caninum* SRS2, *Neospora Caninum* SAG1 and *Fasciola hepatica* Cathepsin L1. Substrates with any two, three, four, five, six, seven, eight or nine antigen combinations of these are suitable. Preferred substrates of the current invention include those which have immobilized thereon the antigens:

a) NS3 and Erns
b) gB and gE
c) SRS2 and SAG1
d) PPA and Cathepsin L1
e) NS3, Erns and LipL32
f) gB, gE and LipL32
g) SRS2, SAG1 and LipL32
h) SRS2, SAG1 and Cathepsin L1
i) NS3, Erns, gB and gE
j) NS3, Erns, SRS2 and SAG1
k) gB, gE, SRS2 and SAG1
I) NS3, Erns, gB, gE and PPA
m) NS3, Erns, gB, gE and SRS2 and SAG1
n) NS3, Erns, SRS2, SAG1 and LipL32
o) NS3, Erns, gB, gE, PPA, LipL32, SRS2, SAG1 and Cathepsin L1.

In further embodiments, the substrate of the invention may also include, in addition to or as a replacement for Erns, an immobilized BVDV E2 antigen. Further still, substrates of the current invention may include additional immobilized antigens to a *Salmonella* species, for example at least one of *Salmonella* dublin or *Salmonella* typhimurium.

The substrates of the current invention may be tailored to specific pathogen groups. For example, a bovine reproductive pathogen array could comprise a substrate with immobilized antigens for BVDV, BoHV-1, a *Leptospira* species, *Neospora caninum* along with immobilized antigens to further pathogens causing reproductive disorders such as *Coxiella burnetti* and Brucellosis. A bovine respiratory pathogen array could comprise a substrate with immobilized antigens to BVDV, BoHV-1 along with immobilized antigens to further pathogens causing respiratory disorders such as Bovine Respiratory Syncytical Virus (BRSV), Parainfluenza virus type 3 (PI3V) and *Mycoplasma bovis*. A bovine enteric pathogen array could comprise a substrate with immobilized antigens for Paratuberculosis and *Fasciola hepatica* along with immobilized antigens to further pathogens causing enteric disorders such as *Salmonella* species or Coronavirus species. A bovine parasite array could comprise a substrate with immobilized antigens to *Neospora caninum* and *Fasciola hepatica* along with immobilized antigens to further parasites such as *Ostertagia ostertagi* and *Dictyocaulus viviparous*.

The "antigens" of the current invention can be any proteins or fragments thereof from the target pathogens which may induce an immune response in an infected animal. The skilled person will understand that recombinant or mutated versions of these may be suitable, and in some cases advantageous, as capture antigens in an ELISA format. Data presented in the current application was generated using recombinant protein capture antigens except for the antigens used for MAP which were sterile, filtered and lyophilized protoplasmic cell extract from *Mycobacterium* spp. The capture antigen used for *Fasciola hepatica* was an inactivated recombinant Cathepsin L1 variant Gly[26].

Preferably the antigens are immobilized on the surface of the substrate, preferably covalently immobilized. The substrate can be any substance able to support one or more antigens, but is preferably a solid-state device, such as a biochip. A biochip is a planar substrate that may be, for example, mineral or polymer based, but is preferably ceramic.

Preferably, a solid-state device is used in the methods of the present invention, preferably the Biochip Array Technology system (BAT) (available from Randox Laboratories Limited). More preferably, the Evidence Evolution, Evidence, Evidence Investigator and MultiSTAT apparatus (available from Randox Laboratories) may be used to determine the presence or absence of antibodies in the sample.

The antigens or fragments thereof of the current invention, are immobilized to a multiplexing system comprising one or more support substrates. The support substrate may comprise a solid-state device, such as a planar surface, bead, or microparticle, upon which is immobilized an antigen or fragment thereof. Such antigens may be immobilized at discrete areas of an activated surface of the support substrate. Alternatively, antigens may be immobilized to discrete support substrates, wherein the discrete support substrates are combined to form a multiplexing system. The solid-state device may perform multi-analyte assays such that the presence or absence of multiple target antibodies in the sample isolated from the subject are determined in parallel. In this context, the support substrate may be one that is used conventionally in multi-analyte microarray technologies. It may, for example, be a biochip, glass slide or other conventional planar support material, or bead or microparticle. The support substrate may be defined as a Discrete Test Area (DTA), which defines the whole substrate, e.g. a single biochip is a DTA. DTAs are physically distinct areas between which liquid or sample flow is not possible. Within each DTA, there may be a plurality of Discrete Test Regions (DTRs, as referred to herein as discrete reaction zones) present. These define discrete locations on a substrate and support antigens or fragments thereof. Each DTR is spatially separated from other DTRs, and each may be used for the same or different reactions, depending on how the reactions are to be performed. The DTRs are usually present within a "biochip", and multiple biochips may be present on the device, each biochip being physically separated from other biochips. In this embodiment, the solid-state device has a multiplicity of DTRs each bearing a desired binding molecule (capture antigen) covalently bound to the substrate, and in which the surface of the substrate between the DTRs is inert with respect to the target antibody under study. The solid-state, multi-analyte device may therefore exhibit little or no non-specific binding. Different binding molecules or antigens may be located in spatially separate locations i.e. within DTRs on the DTA or biochip. In a particular example, the DTA is approximately 1 $cm^2$ and there may be 4×4 DTRs present within each DTA, preferably 5×5 DTRs, 7×7 DTRs, 8×8 DTRs, 9×9 DTRs, 10×10 DTRs, 12×12 DTRs, 15×15 DTRs, 20×20 DTRs, 30×30 DTRs or greater present within each DTA. Alternatively, the multiplexing system may comprise two or more discrete support substrates, each support substrate supporting antigens of a single pathogen or where each discrete support substrate supports an individual antigen, or peptide fragment thereof. The support substrates can be any solid matter which can support pathogen antigens. Non-limiting examples of such are beads, microparticles etc. Thus, a multiplexing system in the context of the current multi-pathogen detecting invention includes any system capable of the concurrent or simultaneous binding and/or detection of antibodies to two, three, four, five, six, seven, eight or nine, or more pathogens. 'Concurrent' means occurring within a similar time frame this time frame is usually within 30 minutes, preferably within 15 minutes, more preferably within 5 minutes. The concurrent or simultaneous binding and detection of analytes is one of principal advantages of a multiplex analysis system.

In one embodiment, each DTR within a DTA may contain immobilized thereto a distinct antigen or fragment thereof. Thus, an indirect assay can be employed to determine the presence of multiple antibodies within the biological sample. In this embodiment, the bovine sample to be analysed may be incubated with the bound antigens. The principle of the assay dictates that antibodies present within the bovine sample will bind to antigens immobilized to the discrete DTRs which they have cross-reactivity to. After a sufficient time to allow binding events to occur, unbound bovine sample can be removed from the DTA by washing and the conjugate containing the labelled detection antibodies can be added. After further incubation and wash steps binding between the labelled detection antibodies and any bovine antibodies which have bound to the immobilized antigens at discrete DTRs can be visualized. The degree of binding can inform as to the presence or concentration of pathogen specific antibodies within the bovine sample. The more antibodies to a pathogen contained within the sample, the more binding is visualized at discrete DTRs upon which the pathogen antigen is immobilized.

A multiplexing substrate of the present invention may be prepared by activating the surface of a suitable substrate, and applying an array of binding molecules (capture antigens), or fragments thereof, on to discrete sites on the surface. If desired, the other active areas may be blocked. The binding molecules or fragments thereof, and blocking agents may be bound to the substrate via a linker. In particular, it is preferred that the activated surface is activated using an organosilane or polymer coating before reaction with the binding agent. The solid-state device used in the methods of the present invention may be manufactured according to the method disclosed in, for example, GB-A-2324866 the contents of which is incorporated herein in its entirety. Preferably, the solid-state device used in the methods of the present invention is the Biochip Array Technology system (BAT) (available from Randox Laboratories Limited). More preferably, the Evidence™, the Evidence Evolution™, Evidence Investigator™ and MultiSTAT apparatus (available from Randox Laboratories) may be used to determine the levels of antibodies in a sample.

The multiplexing system of the present invention may further provide semi-quantitative information as to the differences between the concentrations of antibodies within a sample as compared to a control. For example, antibody levels within a bovine sample may be compared to the antibody levels within a control. The control may be a negative control containing no target antibodies or a positive control containing a known amount of target antibodies to a specific pathogen. In one example, samples are interpreted as being positive or negative based on their ratio against a positive control. Means for converting chemical, fluorescent, or radioactive signals originating from the binding of a probe to a target are well known to the skilled artisan. By way of example, and not limitation, antibody concentrations within a sample may be calculated from a calibration curve constructed from a series of known concentrations of antibody standards. Preferably the standards are detected using the same detectable label as is present on the anti-bovine antibody detection probe(s). Preferably, the calibration curve is constructed at the same time on the same DTA. By way of example and not limitation, the calibration curve may be constructed from a series of known concentrations of an antibody standard calibration curve may be constructed by spiking the biological sample under analysis with the antibody standards.

An advantage of some of the methods and substrates mentioned above is in differentiating infected from vaccinated animals (DIVA) when used in conjunction with certain vaccines. For example, provided herein is a method for DIVA comprising contacting a bovine sample with a substrate comprising the immobilized target antigens NS3 and Erns or glycoprotein B and glycoprotein E, or all four antigens, washing off unbound sample and detecting any antibodies in the sample which are bound to the immobilized antigens on the substrate using a labelled detector antibody. The most common vaccines for IBR are gE negative vaccines and so detecting this antibody in vaccinated herds suggested a naturally acquired infection is present. Current assays require the use of 2 separate singleplex ELISA tests e.g. IBR gB and IBR gE.

Also provided is a method for screening a bovine sample for antibodies to *Mycobacterium* paratuberculosis comprising (a) contacting the bovine sample with a substrate onto which is immobilized an antigen of *M. paratuberculosis*; and an assay buffer containing *Mycobacterium phlei* (b) washing off unbound sample (c) detecting any antibodies in the sample which are bound to the immobilized antigen on the substrate using a labelled detector antibody, wherein said method does not require a sample *M. phlei* pre-absorption step prior to carrying out the method.

Also provided is a method for detecting antibodies to *Mycobacterium* paratuberculosis and at least one other pathogen in a bovine sample, said method comprising (a) contacting the bovine sample with a substrate onto which is immobilized an antigen of *Mycobacterium* paratuberculosis and an antigen of at least one other pathogen; and an assay buffer containing *Mycobacterium phlei*, (b) washing off unbound sample (c) detecting any antibodies in the sample which are bound to the immobilized antigen on the substrate using a labelled detector antibody, wherein said method does not require a sample *M. phlei* pre-absorption step prior to carrying out the method. Preferably, the at least one other pathogen is selected from the list comprising; Bovine Viral Diarrhoea Virus (BVDV), Bovine Herpesvirus-1 (BoHV-1), a *Leptospira* species, *Neospora caninum* and *Fasciola* hepatica.

Figure 2:
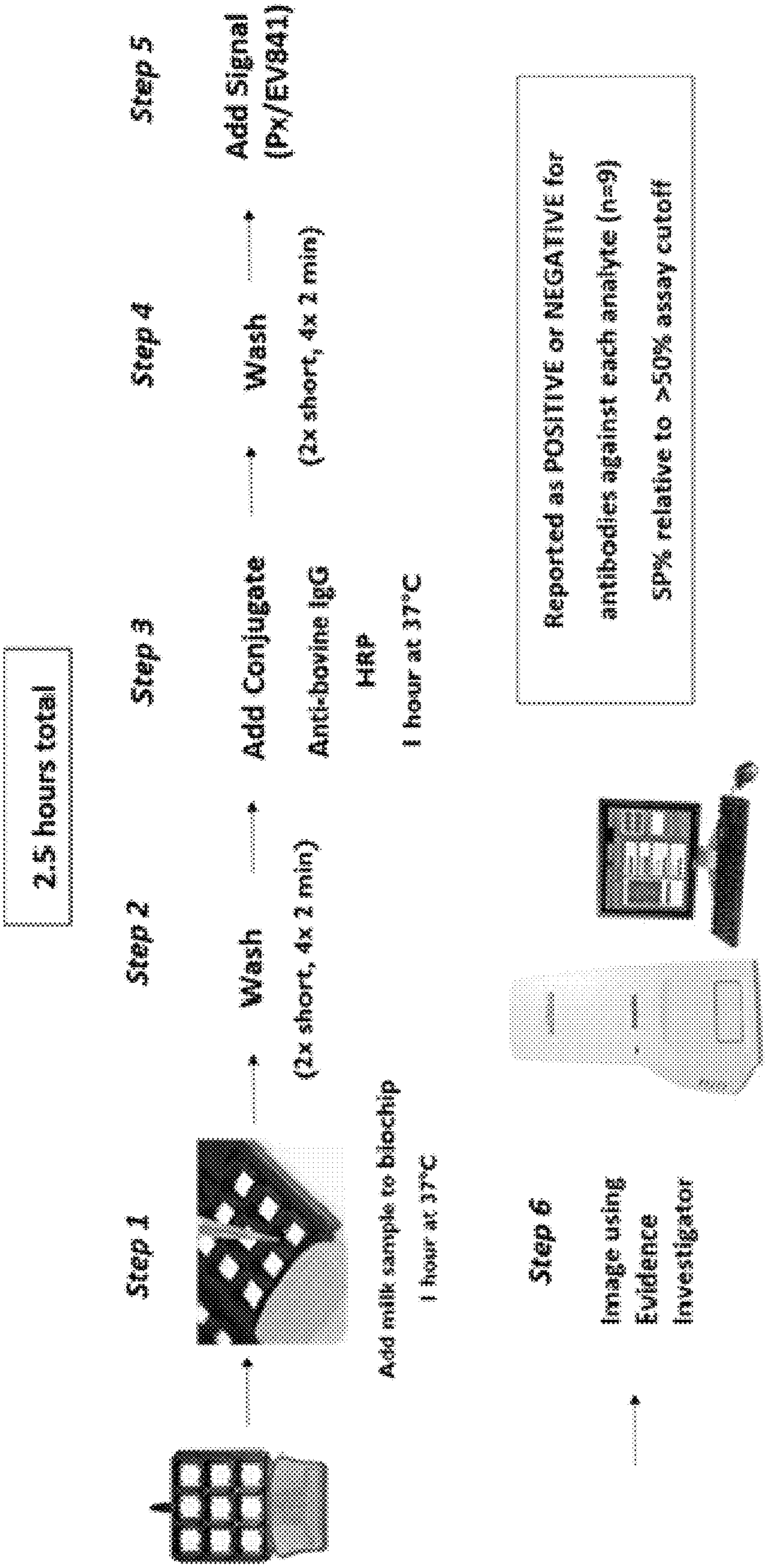
FIG. 2 Example assay protocol for the Bovine pathogen array carried out on the Evidence Investigator (Randox Laboratories Ltd, Crumlin, Northern Ireland). The total assay time is 2.5 hrs.

The advantage of these novel methods is that there is no requirement for a sample *Mycobacterium Phlei* pre-absorption step, thereby making the current assay more efficient than existing assays. All available commercial ELISA kits have a sample pre-absorption step with *Mycobacterium phlei* antigens to enhance assay specificity by limiting cross-reactions with mycobacteria other than *Mycobacterium avium* Subspecies Paratuberculosis. *Mycobacterium phlei* is an intricate component of the bovine pathogen array assay buffer, hence there is no requirement for a separate sample pre-absorption step. This sample preabsorption step can take anything up to 2 hours. As well as requiring a preabsorption step, no commercial ELISAs are in a multiplex format. The inclusion of *M. Phlei* in the buffer herein did not have any negative effect on the assay performance and was compatible with the novel multiplex format. The assay buffer containing *M. phlei* is added along with the sample in the first incubation step of the methods of the current application (Step 1, FIG. 2). Any suitable assay buffer as known to the skilled person may be used.

The current application also provides a kit comprising a substrate onto which is immobilized an antigen of *Mycobacterium* paratuberculosis and optionally an antigen of at least one other pathogen; and an assay buffer containing *Mycobacterium phlei*. Preferably, the at least one other pathogen is selected from the list comprising; Bovine Viral Diarrhoea Virus (BVDV), Bovine Herpesvirus-1 (BoHV-1), a *Leptospira* species, *Neospora caninum* and *Fasciola hepatica* and preferably the antigen is selected from the list consisting of BVDV N53, BVDV Erns, BoHV-1 glycoprotein B, BoHV-1 glycoprotein E, MAP PPA, *Leptospira* hardjo LipL32, *Neospora caninum* SRS2, *Neospora caninum* SAG1 and *Fasciola hepatica* Cathepsin L1.

A final aspect of the current invention is a multiplex assay normalisation method to enable ease of result interpretation for the end user. Said method comprises normalising the results for all analytes in the array to a >50% assay cut-off for each test. A variety of different cut-offs ranging from >15%, 25%, >30%, >35%, >50%, >60% etc could be used as along as the same cut-off is applied to all results in the multiplex assay. This is enabled by using a predetermined multiplication factor which is specific to each batch of positive controls. The multiplication factor can be based on the assay output of a master positive control batch in comparison to the assay cut-off threshold (Table 4). For example, the assay output could be relative light units (RLU). This can be automatically carried out in a result workbook (for example a Microsoft Excel spreadsheet) provided with the assay which can present results not only as a simple positive and negative for each analyte but also reveal how positive or negative samples are compared to the controls. Results of ELISA based tests are usually reported based on the cut-offs which have been established for that particular assay. When running multiple tests with various cut-offs it can be difficult to ascertain just how positive or negative a sample is and the current method simplifies this for the end user. A further advantage of this normalisation method is that since the results are normalised to a master batch of positive controls it removes batch to batch variance issues. Inter-analyser variance which could be a problem if using standard cut-offs can also be eliminated. The skilled person will understand that such a method could be applicable to all multiplex assays. In the example of a Bovine pathogen array, such a multiplex assay normalisation method has a number of advantages. As well as ease of interpretation of results for multiple pathogens, the additional information of the percentage positivity or negativity of each sample compared to controls has the potential to indicate stage of infection, influence treatment pathways and enable the identification of animals requiring follow-up tests or monitoring.

A high percentage positive for one pathogen can be interpreted differently than for another. For example, the SP % can indicate the stage of infection (as the incubation periods for some of these pathogens may differ) and also the extent/severity of disease for the different pathogens.

The SP % can also be very important in determining the disease outcome as for some of these pathogens animals will recover if they receive timely and appropriate treatment e.g. *Fasciola hepatica* however for other pathogens e.g. MAP treatment is largely not successful and in the majority of cases if a positive animal is identified it will be euthanized in order to prevent any further disease spread within the herd.

As with competitor single-plex antibody detection tests, it is envisaged that the Bovine Pathogen Array will largely be used for surveillance in dairy herds to monitor antibody levels in individual and bulk milk samples over time. A bulk milk sample refers to a pooled milk sample collected from the whole herd.

A value 50% for any analyte is reported as negative in the bovine pathogen array. This result could be indicative that an animal/herd has never been exposed to the infectious agent or that perhaps any previous exposure which may have happened was not recent and that antibody levels have declined below the cut-off level. Such a negative result would not be a concern and individual animals or herds would not require treatment by a farmer/vet.

A number of dairy herd health schemes have been established in various countries and these involve testing bulk milk samples collected from herds every 3 months (4 samples collected per year). The regulatory body Cattle Health Certification Standards have accredited a number of such schemes in the UK and Ireland including the National Milk laboratories BVD HerdCheck scheme.

Bulk milk results obtained are compared against previous results and if a significant increase in antibody level against a particular pathogen occurs between two time points which would be indicative of recent exposure i.e. if a bulk milk sample collected in January had a BVD NS3 SP % value of 12% and another bulk milk sample collected from the same herd in May had a BVD NS3 SP % value of 595% this would suggest recent exposure within the herd. The farmer/veterinary surgeon in charge of herd health could then collect individual samples from all cows within the herd to identify which ones are infected. Infected animals would then be isolated and treated accordingly to prevent extensive disease spread within the whole herd.

Similarly, if a bulk milk sample collected in January had a BVD NS3 SP % value of 12% and another bulk milk sample collected from the same herd in May had a BVD NS3 SP % value of 75% could suggest very recent exposure and the detection of a small number of animals within the herd starting to seroconvert. A follow up test would therefore be advisable, but this would be at the discretion of the farmer/veterinary surgeon in charge of herd health.

Ascertaining how positive an individual or herd sample is could also aid in prioritizing treatments e.g. 51% vs 2000% positivity results could lead to different treatment pathways for these animals.

If testing a bulk milk sample i.e. a pooled sample collected from the whole herd, the higher the percentage SP % may also indicate how extensively the disease has spread and the number of cows within the herd which are affected.

Methods

Selected immunodominant antigens specific to each pathogen were immobilized on defining discrete test regions (DTRs) on the biochip surface. One hundred microliters of milk sample were added to the biochip well containing 200 μl assay buffer and incubated for 1 hour at 37° C. Following two quick washes and four long washes (2-minute soak) with diluted wash buffer, 300 μl of horseradish peroxidase (HRP) conjugated anti-bovine IgG was added to the biochip well and incubated again for 1 hour at 37° C. A repeat washing step (two quick washes and four long washes) preceded the addition of 250 μl signal reagent, containing a 1:1 mixture of luminol/peroxide solution and the biochip was incubated for 2 minutes protected from light. A chemiluminescent signal is produced when HRP-labelled anti-bovine IgG binds to antibody in the sample which is bound to the antigen containing DTRs on the biochip surface. The chemiluminescent signal was detected with digital imaging technology (charged coupled device (CCD) camera, in this case the Evidence Investigator™ system, Randox Laboratories Ltd.) and results were compared to internal assay positive and negative controls. Results were reported as positive or negative. For each sample, a semi quantitative percentage positivity value was provided relative to the positive control.

Results

TABLE 1

Percentage agreement in sample classification between the Bovine pathogen array (BPA) and commercial predicate ELISAs (n = 349)

| Test | Agreement (%) |
|---|---|
| BVD (NS3) | 100% |
| IBR (gB) | 100% |
| IBR (gE) | 100% |
| MAP | 98% |
| *Leptospirosis* | 100% |
| *Neospora caninum* | 100% |
| *Fasciola hepatica* | 100% |

TABLE 2

Enhanced diagnostic performance of the Bovine pathogen array for Infectious bovine rhinotracheitis in comparison to a predicate ELISA using whole virus antigen.

| Sample ID | IBR total array | BPA IBR-gB | BPA IBR-gE |
|---|---|---|---|
| 1 | Positive | Positive | Positive |
| 2 | Negative | Negative | Negative |
| 3 | Positive | Negative | Positive |

TABLE 2-continued

Enhanced diagnostic performance of the Bovine pathogen array for Infectious bovine rhinotracheitis in comparison to a predicate ELISA using whole virus antigen.

| Sample ID | IBR total array | BPA IBR-gB | BPA IBR-gE |
|---|---|---|---|
| 4 | Positive | Positive | Negative |
| 5 | Negative | Negative | Positive |

The BPA demonstrates a DIVA capacity for samples 3-5 compared to when using whole virus antigen. All samples are milk samples.

TABLE 3

Enhanced diagnostic performance of the Bovine pathogen array for Neospora caninum in comparison to a predicate ELISA using crude tachyzoite antigen.

| Sample ID | Tachyzoite antigen | BPA NC-SRS2 | BPA NC-P29 |
|---|---|---|---|
| 6 | Positive | Positive | Positive |
| 7 | Negative | Negative | Negative |
| 8 | Negative | Positive | Negative |
| 9 | Negative | Positive | Positive |

The BPA demonstrates antibody detection at both tachyzoite and bradyzoite stages of infection for samples 8 and 9 compare to when using crude tachyzoite antigen only. All samples are milk samples.

Example 1

The ratio of sample/positive control for each analyte was determined during a large milk study (>300 milk sample for each analyte) and using a master batch of multi-analyte positive controls. As the ratio of sample/positive control was different for each analyte it was decided to normalise the cut-off for each analyte to a >50%. This involved the assignment of multiplication factors required for the >50% assay threshold. The required multiplication factors are imbedded in the result formula above.

TABLE 4

An example of the normalisation to >50% assay threshold.

| Analyte | Cut off threshold | Master Positive control RLU | Ratio sample/ positive control | Multiplication factor required to normalise to >50% assay threshold |
|---|---|---|---|---|
| NS3 | >1964 | 4782 | >41% = positive | 1.21951 |
| MAP PPA | >558 | 3858 | >14% = positive | 3.571428 |

The assay threshold for each analyte/batch of positive controls for the bovine pathogen array will always be >50%. When a new batch of multi-analyte controls is prepared these are run alongside the master multi-analyte control batch for which the ratio sample/positive control and multiplication factor was determined. Any difference in multi-analyte control batches will be accounted for in the multiplication factor assigned to each multi-analyte control batch—see example below.

The formula used to calculate the sample positivity percentage (SP %) is as follows:

Sample RLU×100=SP % (×Multiplication factor)

Positive Control RLU

Analyte: NS3

Master batch positive control: 2288 RLU

Normalisation to 50%=multiplication factor of 2.9 [50/17.4=2.9]

Control batch 2: 2500 RLU (↑212 RLU=↑9.27%)

Normalisation to 50%=2.9*1.0927%=mf of 3.17

Sample A: 2311 RLU

Control batch 1=2311/2288*100*2.90=293% (positive)

Control batch 2=2311/2500*100*3.17=293% (positive)

Competitor ELISAs for each of the pathogens typically apply a variety of different cut-offs ranging from >15%, 25%, >30%, >35%, >50%, >60% etc. A >50% cut-off was selected and applied to all assays included in the Bovine Pathogen Array for ease of result interpretation by the end user i.e. if the following results were obtained for 2 particular samples it is easier to classify results as positive or negative and interpret how positive a sample is for sample 1 versus sample 2 where a range of different assay cut-offs are applied.

TABLE 5

Result comparison using a >50% cut-off

| | BVD NS3 | BVD Erns | IBR gB | IBR gE | MAP | Hardjo LipL32 | NC SRS2 | NC P29 | FHCL1 |
|---|---|---|---|---|---|---|---|---|---|
| Sample 1 | 687% | 550% | 10% | 12% | 5% | 152% | 75% | 251% | 1028% |
| Cut-off | >50% | >50% | >50% | >50% | >50% | >50% | >50% | >50% | >50% |

TABLE 6

Result comparison using a variety of different cut-offs

| | BVD NS3 | BVD Erns | IBR gB | IBR gE | MAP | Hardjo LipL32 | NC SRS2 | NC P29 | FHCL1 |
|---|---|---|---|---|---|---|---|---|---|
| Sample 2 | 18% | 62% | 97% | 14% | 269% | 75% | 158% | 158% | 10% |
| Cut-off | >35% | >60% | >33% | >15% | >35% | >50% | >25% | >30% | >12.5% |

The SP % values included for sample 1 and 2 above are only example values and are not relative to one another.

The invention claimed is:

1. A substrate comprising BVDV NS3, BVDV Erns, BoHV-1 glycoprotein B, and BoHV-1 glycoprotein E antigens, wherein the substrate is a biochip.

2. The substrate of claim 1, further comprising a BVDV E2 antigen immobilized onto the substrate.

3. The substrate of claim 1, further comprising an antigen from at least one of *Salmonella* Dublin or *Salmonella Typhimurium* immobilized onto the substrate.

4. A method for screening a bovine sample for antibodies against two or more pathogens, said method comprising; (a) contacting the bovine sample with a substrate of claim 1, 2 or 3; (b) washing off unbound sample; and (c) detecting any antibodies in the sample which are bound to the immobilized antigens on the substrate using a labelled detector antibody.

5. The method of claim 4, wherein the detector antibody is an anti-IgG or anti-IgM antibody.

6. The method of claim 5, wherein the detector antibody is labelled with Horseradish peroxidase (HRP).

7. The method of claim 4, wherein the bovine sample is serum, plasma or milk.

* * * * *